(12) United States Patent
Ferro et al.

(10) Patent No.: US 9,629,641 B2
(45) Date of Patent: Apr. 25, 2017

(54) RASP

(71) Applicant: AOD Holdings, LLC, Arroyo Grande, CA (US)

(72) Inventors: Thomas D. Ferro, Arroyo Grande, CA (US); Joe Phillips, Arroyo Grande, CA (US); Donald Lee, Arroyo Grande, CA (US); John Park, Arroyo Grande, CA (US); Austin T. Ferro, Arroyo Grande, CA (US)

(73) Assignee: AOD Holdings, LLC, Arroyo Grande, CA (US)

(*) Notice: Subject to any disclaimer, the term of this patent is extended or adjusted under 35 U.S.C. 154(b) by 427 days.

(21) Appl. No.: 14/315,341

(22) Filed: Jun. 26, 2014

(65) Prior Publication Data
US 2015/0005777 A1      Jan. 1, 2015

Related U.S. Application Data

(60) Provisional application No. 61/839,613, filed on Jun. 26, 2013.

(51) Int. Cl.
*A61B 17/16* (2006.01)

(52) U.S. Cl.
CPC .......... *A61B 17/1659* (2013.01); *A61B 17/16* (2013.01); *A61B 17/1622* (2013.01); *A61B 17/1624* (2013.01); *A61B 17/1628* (2013.01); *A61B 17/1668* (2013.01); *A61B 17/1675* (2013.01); *A61B 17/1684* (2013.01)

(58) Field of Classification Search
CPC . A61B 17/16; A61B 17/1622; A61B 17/1624; A61B 17/1628; A61B 17/1659; A61B 17/1668; A61B 17/1675; A61B 17/1684; B23C 2210/326; B23D 7/10; B23D 2015/007; B23D 49/003; B23D 49/005; B23D 49/006; B23D 67/02; B23D 67/04; B23D 71/04; B23D 71/08; B23D 79/06
See application file for complete search history.

(56) References Cited

U.S. PATENT DOCUMENTS

| | | | | |
|---|---|---|---|---|
| 6,007,541 A | * | 12/1999 | Scott | A61B 17/148 30/369 |
| 8,002,776 B2 | * | 8/2011 | Liu | A61B 17/1659 606/85 |
| 8,388,622 B2 | * | 3/2013 | Narducci | A61B 17/1624 606/85 |
| 8,393,409 B2 | * | 3/2013 | Pedicini | A61B 17/92 173/109 |

* cited by examiner

*Primary Examiner* — Larry E Waggle, Jr.

(57) ABSTRACT

A rasp for shaping a bone is provided. The rasp includes a housing, a driving mechanism, a first gear assembly, two linkage units and two blades. The housing has a channel along a first axis. The driving mechanism has an output gear rotating about the first axis. The first gear assembly rotates about a second axis and is driven by the output gear. The first gear assembly has a first and a second rotation surfaces. A first and a second connection points are respectively located on the first and the second rotation surfaces. The linkage units slidably pass through the channel. The first end of each of the linkage units is pivotally connected to the corresponding connection point, such that the second ends move along the first axis in a reciprocating manner. The blades are respectively and detachably connected to the second ends.

15 Claims, 11 Drawing Sheets

RASP

RELATED APPLICATIONS

This application claims priority to U.S. Provisional Application No. 61/839,613, filed Jun. 26, 2013, which is herein incorporated by reference.

BACKGROUND

Technical Field

The present disclosure relates to rasps. More particularly, the present disclosure relates to rasps for shaping bones for receiving a prosthesis.

Description of Related Art

Prior to inserting a prosthesis in a bone, and in particular a prosthesis in the top end of a femur, the surgeon must prepare the medullary cavity of the bone so as to give it a shape which is complementary to the shape of the prosthesis. This is done by using a rasp which includes a handle for gripping and a toothed blade whose shape corresponds to the shape of the prosthesis. The teeth on the blade are sharp, thereby enabling them to scrape away the surrounding spongy bone, much like a file.

Surgical ablating tools for use in the resection of bone and tissue during surgical procedures are common. Inventions in the prior art utilize single blades, offset blades, chisels, and rasps in a variety of configurations. Some utilize a reciprocating action while others use a lateral stroke. Inventions in the prior art also experience a number of problems. The single blade configuration will tend to bind up during a surgical procedure if the speed of the blade is diminished or the teeth of the blade catch on bone or tissue. Some of these designs utilize many gears and other moving parts which can be prone to fail. In addition, the rapid reciprocating action of these power tools can affect the precision of the instrument during operation. Therefore, a tool which can smoothly and efficiently ablate bone and spongy tissue, and can avoid binding and has limited moving parts is highly desired.

SUMMARY

A technical aspect of the present disclosure provides a rasp which exerts null net resultant force on the bone during the shaping of the bone, thus allowing a better control for the surgeon.

According to an embodiment of the present disclosure, a rasp for shaping a bone for receiving a prosthesis is provided. The rasp includes a housing, a driving mechanism, a first gear assembly, two linkage units and two blades. The housing has a channel orientated along a first axis. The driving mechanism has an output gear rotating about the first axis. The first gear assembly is rotatably disposed in the housing to rotate about a second axis and is driven by the output gear. The first gear assembly has a first rotation surface and a second rotation surface opposite to each other. A first connection point and a second connection point are respectively located on the first and second rotation surfaces. The linkage units slidably pass through the channel. Each of the linkage units has a first end and a second end, in which the first end of each of the linkage units is pivotally connected to the corresponding connection point, such that the second ends are driven by the first gear assembly to move along the first axis in a reciprocating manner. The blades are respectively and detachably connected to the second ends.

In one or more embodiments of the present disclosure, the first gear assembly includes a first gear and a second gear. The first gear is rotatably disposed in the housing and is driven by the output gear, such that the first gear rotates in a first direction about the second axis, in which the first rotation surface is located on the first gear. The second gear is rotatably disposed in the housing and is driven by the output gear, such that the second gear rotates in a second direction opposite to the first direction about the second axis, in which the second rotation surface is located on the second gear.

In one or more embodiments of the present disclosure, a rotation locus of the first connection point and a rotation locus of the second connection point are 180 degrees out of phase. When the first gear rotates to locate the first connection point at a nearest position of the first connection point relative to the channel, the second gear rotates to locate the second connection point at a farthest position of the second connection point relative to the channel. When the first gear rotates to locate the first connection point at a farthest position of the first connection point relative to the channel, the second gear rotates to locate the second connection point at a nearest position of the second connection point relative to the channel.

In one or more embodiments of the present disclosure, the first gear and the second gear have a same first pitch center diameter.

In one or more embodiments of the present disclosure, the output gear has a second pitch center diameter smaller than the first pitch center diameter.

In one or more embodiments of the present disclosure, each of the linkage units includes a connecting rod and an arm. Each of the first ends being is located on the corresponding connecting rod. The connecting rods are located between the first gear and the second gear. Each of the arms is connected with the corresponding connecting rod and passes through the channel. Each of the second ends is located on the corresponding arm a from the connecting rods.

In one or more embodiments of the present disclosure, each of the blades has a plurality of grooves parallel to each other. The grooves of one of the blades are slidably engaged with the grooves of another one of the blades.

In one or more embodiments of the present disclosure, each of the blades includes two sub-blades, such that an accommodation space is formed between the sub-blades and along the first axis.

In one or more embodiments of the present disclosure, the driving mechanism includes a power source and a motor. The motor is electrically connected to the power source and includes an output shaft connected to the output gear, so as to drive the output shaft to rotate the output gear.

In one or more embodiments of the present disclosure, the power source is a rechargeable battery.

In one or more embodiments of the present disclosure, the driving mechanism includes a second gear assembly. The second gear assembly includes an input shaft, an annulus gear, an output shaft, a sun gear, a planetary gear platform and a plurality of planet gears. The input shaft is substantially coaxial with the first axis, and is configured to be driven by an external driving device. The annulus gear is connected to the input shaft, in which a center of rotation of the annulus gear is on the first axis. The output shaft is connected to the output gear and coaxial with the first axis. The sun gear is connected to and coaxial with the output shaft. The output shaft passes through the planetary gear platform. The output gear and the sun gear are respectively located at two opposite sides of the planetary gear platform. The planetary gear platform has a plurality of first protruding portions located on the side facing the output gear. The planet gears are rotatably mounted on the planetary gear platform, in which the planet gears are located between the input shaft and the planetary gear platform and between the annulus gear and the sun gear. Each of the planet gears is meshed with the annulus gear and the sun gear.

In one or more embodiments of the present disclosure, the rasp further includes a torque limiter. The torque limiter is connected with the housing and includes a locking plate and an adjustment assembly. The locking plate is located between the output gear and the planetary gear platform, in which the output shaft passes through the locking plate. The locking plate has a plurality of second protruding portions facing the side on which the first protruding portions are located. The adjustment assembly is operatively connected to the planetary gear platform for moving the planetary gear platform towards or away from the locking plate, such that a distance between the locking plate and the planetary gear platform can be adjusted.

In one or more embodiments of the present disclosure, the adjustment assembly includes a first adjustment structure and a second adjustment structure. The first adjustment structure is operatively connected to the planetary gear platform and has a first threaded portion, in which the locking plate is located between the first adjustment structure and the planetary gear platform. The second adjustment structure is rotatably connected with the housing and has a second threaded portion meshed with the first threaded portion, in which the first adjustment structure is located between the locking plate and the second adjustment structure. When the second adjustment structure rotates relative to the housing to move the first adjustment structure towards the locking plate, the planetary gear platform is driven by the first adjustment structure to correspondingly move away from the locking plate. When the second adjustment structure rotates relative to the housing to move the first adjustment structure away from the locking plate, the planetary gear platform is driven by the first adjustment structure to correspondingly move towards the locking plate, so as to adjust the distance.

In one or more embodiments of the present disclosure, the torque limiter further includes a spring and a pushing structure. The spring is located between the first adjustment structure and the locking plate. The pushing structure is located between the spring and the locking plate. The pushing structure includes a base plate and a supporting pillar connected to the base plate, in which the supporting pillar passes through the locking plate and abuts against the planetary gear platform.

In one or more embodiments of the present disclosure, the rasp further includes an adaptor connected to the housing. The adaptor is configured to engage with the external driving unit and the external driving unit drives the input shaft to rotate relative to the housing.

When compared with the prior art, the embodiments of the present disclosure mentioned above have at least the following advantages:

(1) In the embodiments of the present disclosure, the linkage units are driven by the first gear assembly to move along the channel in a reciprocating manner. Therefore, the two blades respectively connected to the linkage units are driven to move in a reciprocating manner as well. In this way, during an operation, the forces acting on the bone by each of the two blades cancel out with each other, such that the net resultant force acting on the bone by the rasp is zero. As a result, the surgeon can have a better control over the use of the rasp. Consequently, the safety of operation is obviously increased.

(2) In the embodiments of the present disclosure, there are only a small number of moving parts involved. Thus, the chance that any of the moving parts gets failed is low, and the maintenance time and cost of the rasp is significantly decreased.

(3) In the embodiments of the present disclosure, the output gear has a second pitch center diameter smaller than the first pitch center diameters of the first gear and the second gear. Therefore, the forces acting on the linkage units respectively by the first gear and the second gear are increased in magnitude while decreased in speed relative to the output gear. As a result, the surgeon can have a better control over the use of the rasp. Consequently, the safety of operation is obviously increased.

(4) In the embodiments of the present disclosure, the linkage units slidably pass through the channel. Thus, the reciprocating movements of the linkage units along the sliding direction can be simply guided by the channel. In addition, each of the blades has a plurality of grooves parallel to each other, and the grooves of one of the blades are slidably engaged with the grooves of another one of the blades. As a result, the risk that the two blades have lateral movements with each other is safely avoided.

BRIEF DESCRIPTION OF THE DRAWINGS

The disclosure can be more fully understood by reading the following detailed description of the embodiments, with reference made to the accompanying drawings as follows.

DETAILED DESCRIPTION

Figure 1:
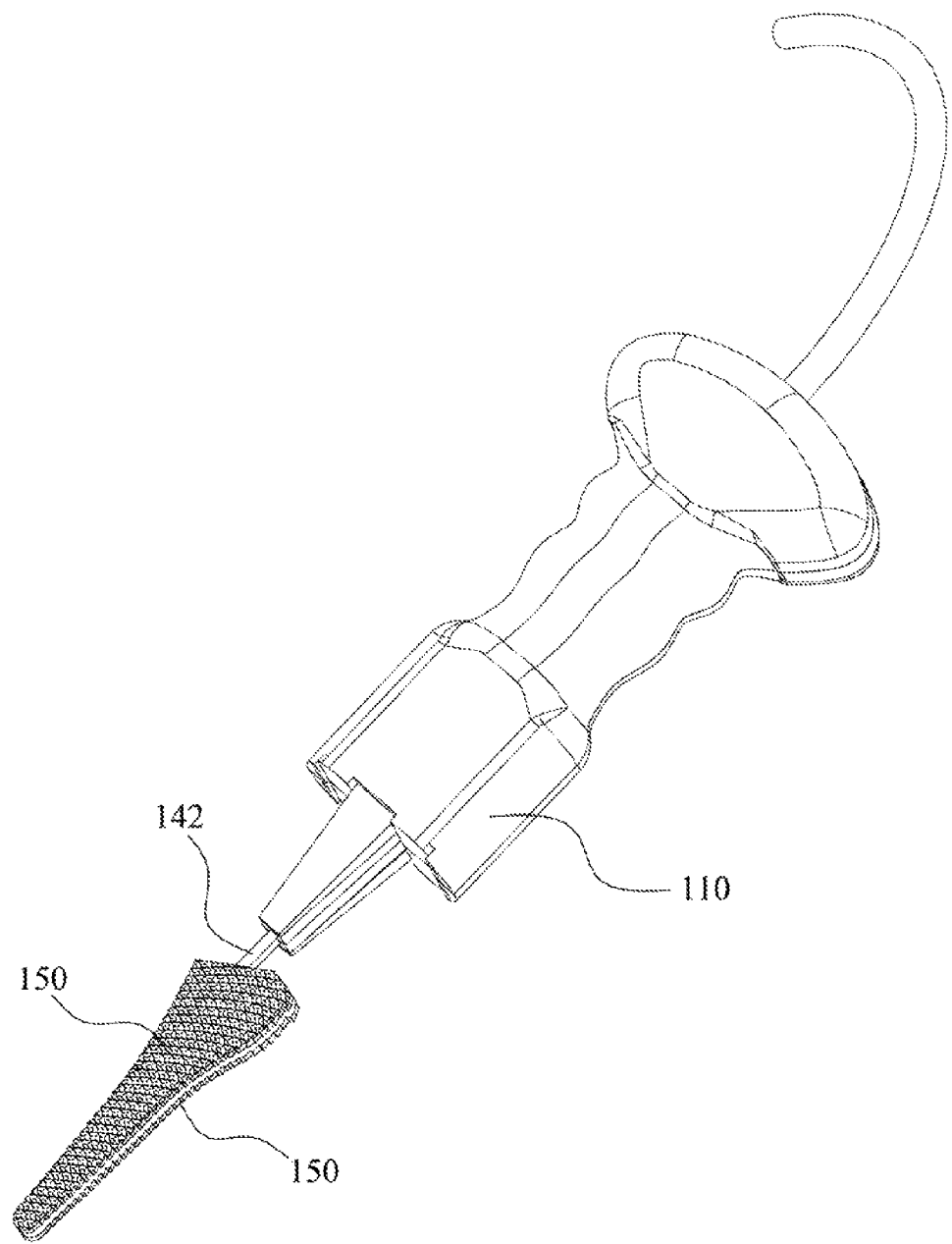
FIG. 1 is a perspective diagram of a rasp according to an embodiment of the present disclosure.

Drawings will be used below to disclose a plurality of embodiments of the present disclosure. For the sake of clear illustration, many practical details will be explained together in the description below. However, it is appreciated that the practical details should not be used to limit the claimed scope. In other words, in some embodiments of the present disclosure, the practical details are not essential. Moreover, for the sake of drawing simplification, some customary structures and elements in the drawings will be schematically shown in a simplified way. Wherever possible, the same reference numbers are used in the drawings and the description to refer to the same or like parts.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2:
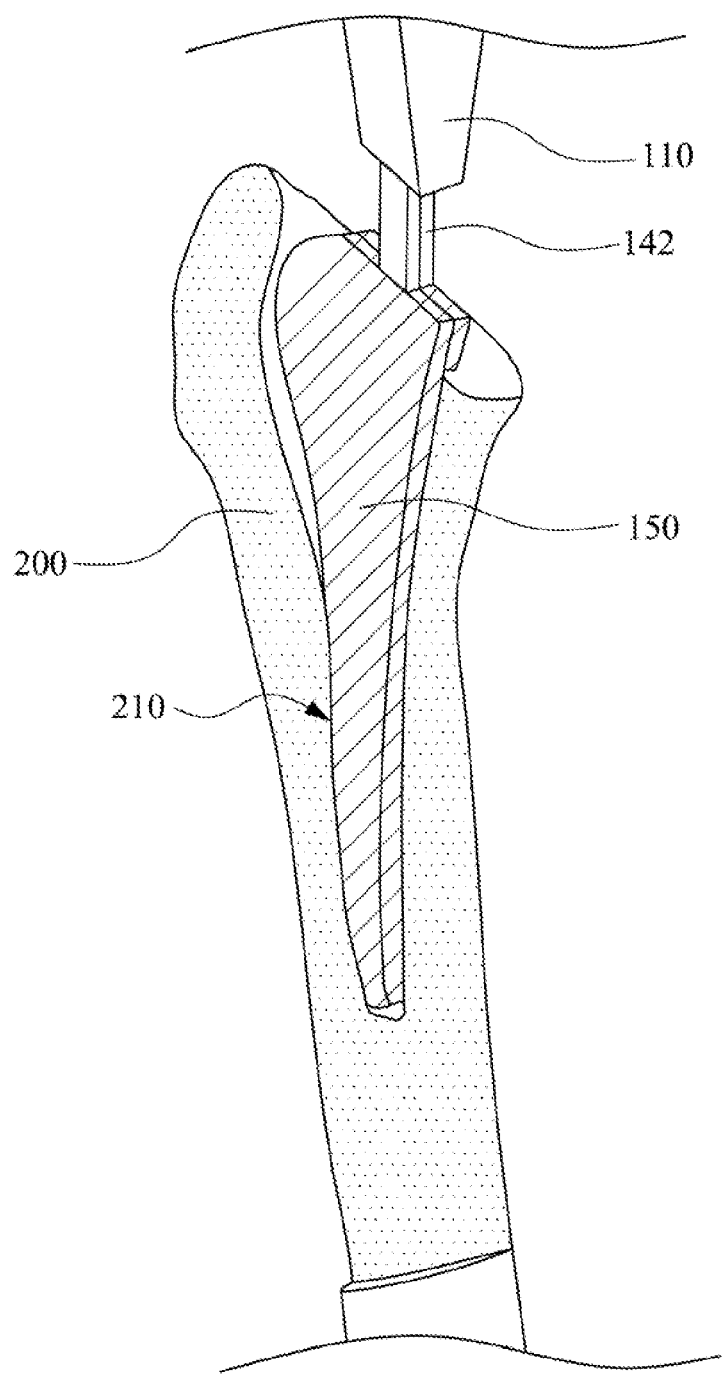
FIG. 2 is a schematic diagram of the rasp of FIG. 1, illustrating the scenario the rasp is forming a medullary canal in a bone.
Figure 3:
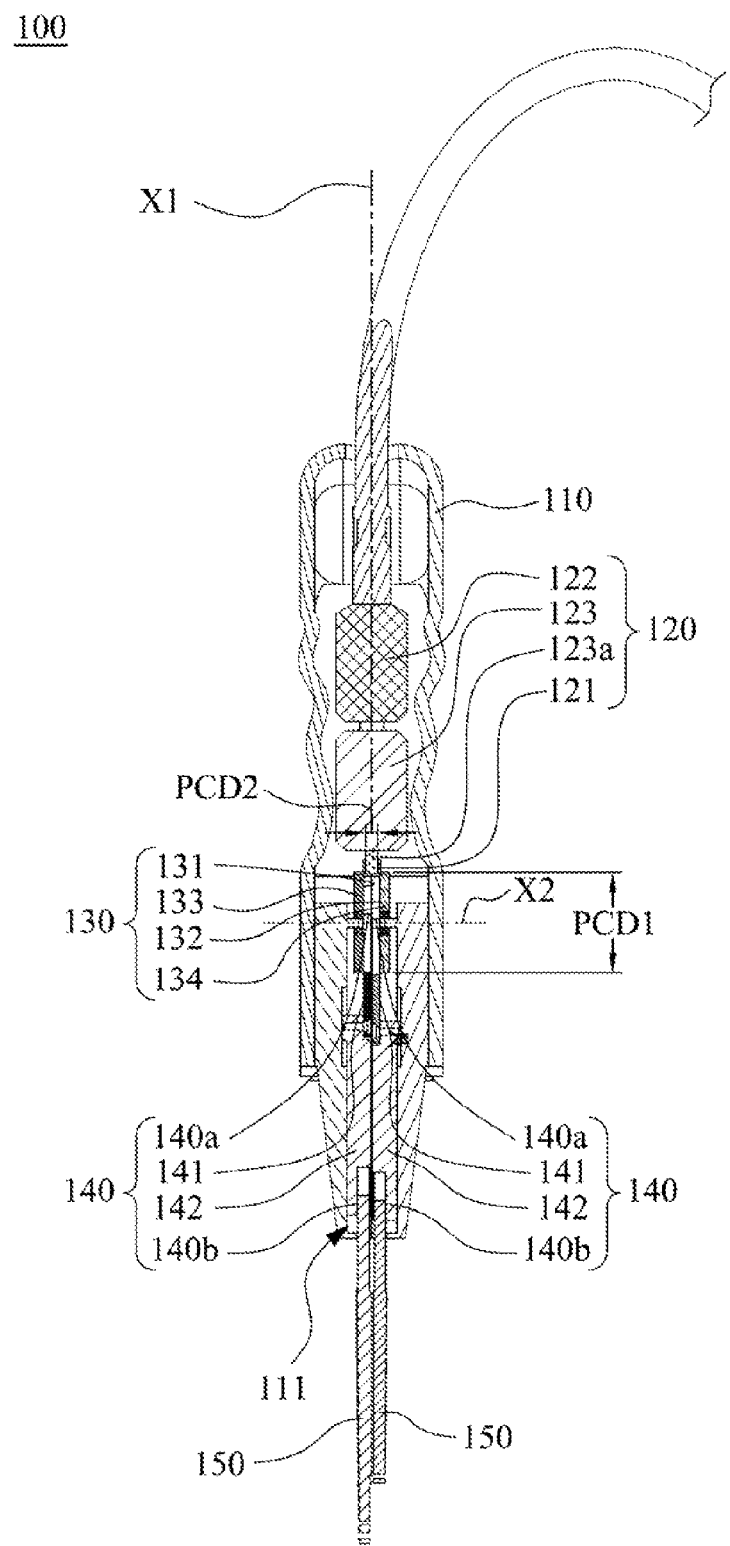
FIG. 3 is a sectional view of the rasp of FIG. 1.
Figure 4:
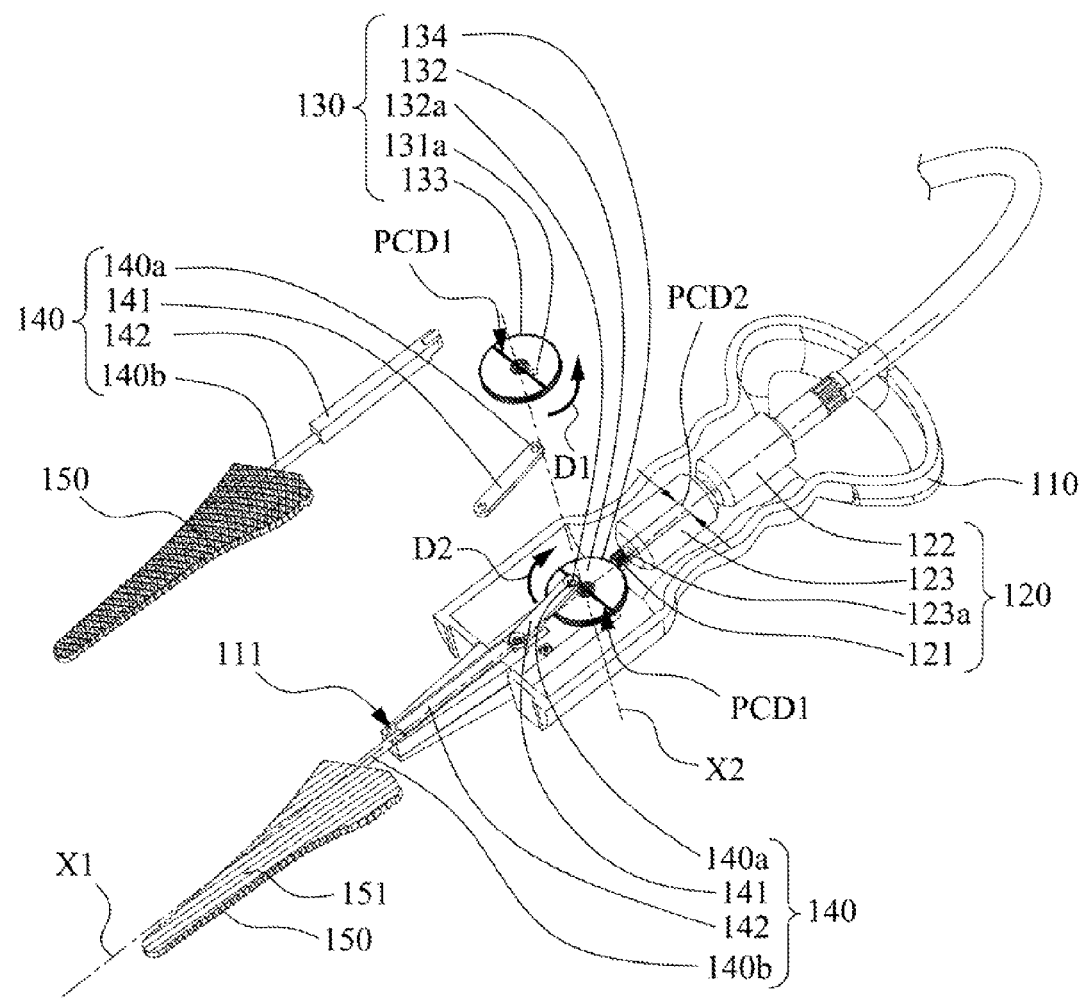
FIG. 4 is a partially exploded perspective view of the rasp of FIG. 1.

FIG. 1 is a perspective diagram of a rasp 100 according to an embodiment of the present disclosure. FIG. 2 is a schematic diagram of the rasp 100 of FIG. 1, illustrating the scenario the rasp 100 is forming a medullary canal 210 in a bone 200. FIG. 3 is a sectional view of the rasp 100 of FIG. 1. FIG. 4 is a partially exploded perspective view of the rasp 100 of FIG. 1. As shown in FIGS. 1-4, the rasp 100 for shaping the bone 200, or more specifically forming the medullary canal 210 of the bone 200 for receiving a prosthesis (not shown) is provided. The rasp 100 includes a housing 110, a driving mechanism 120, a first gear assembly 130, two linkage units 140 and two blades 150. The housing 110 has a channel 111 orientated along a first axis X1. The driving mechanism 120 has an output gear 121 rotating about the first axis X1. The first gear assembly 130 is rotatably disposed in the housing 110 to rotate about a second axis X2 and is driven by the output gear 121. The second axis X2 is substantially perpendicular to the first axis X1. However, this does not limit the present disclosure. The first gear assembly 130 has a first rotation surface 131 and a second rotation surface 132 opposite to each other. A first connection point 131a and a second connection point 132a are respectively located on the first rotation surface 131 and second rotation surface 132. The linkage units 140 slidably pass through the channel 111. Each of the linkage units 140 has a first end 140a and a second end 140b, in which the first end 140a of each of the linkage units 140 is pivotally connected to the corresponding connection point 131a or 132a, such that the second ends 140b are driven by the first gear assembly 130 to move along the first axis X1 in a reciprocating manner. The channel 111 provides guidance to the sliding movement of the linkage units 140. Moreover, the blades 150 are respectively and detachably connected to the second ends 140b.

To be more specific, the rasp 100 is intended for use in hip arthroplasty. A total hip arthroplasty, or hip hemiarthroplasty, is a procedure that is performed to alleviate pain from arthritis, or to correct joint damage as part of a hip fracture treatment. Hip arthroplasty is currently the most common orthopedic operation. By using the rasp 100, a suitable medullary canal 210 in the bone 200, the proximal femur in this case, is created such that the proximal femur can receive a femoral hip stem prosthesis. In general, the shape of the blades 150 corresponds to the shape of the prosthesis to be implanted.

As shown in FIGS. 3-4, the first gear assembly 130 includes a first gear 133 and a second gear 134. The first gear 133 is rotatably disposed in the housing 110 and is driven by the output gear 121, such that the first gear 133 rotates in a first direction D1 about the second axis X2, in which the first rotation surface 131 is located on the first gear 133. The second gear 134 is rotatably disposed in the housing 110 and is driven by the output gear 121, such that the second gear 134 rotates in a second direction D2 opposite to the first direction D1 about the second axis X2, in which the second rotation surface 132 is located on the second gear 134. To achieve the balance of the first gear assembly 130, the first gear 133 and the second gear 134 have the same first pitch center diameter PCD1. Moreover, the output gear 121, the first gear 133 and the second gear 134 can be in the form of beveled gears. However, this form of the first gear 133 and the second gear 134 does not limit the present disclosure.

As shown in FIG. 4, the locations of the first connection point 131a and the second connection point 132a are relatively opposite to each other with respect to the second axis X2. In other words, the rotation locus of the first connection point 131a located on the first rotation surface 131 and the rotation locus of the second connection point 132a located on the second rotation surface 132 are 180 degrees out of phase. When the first gear 133 rotates to locate the first connection point 131a at a nearest position of the first connection point 131a relative to the channel 111, the second gear 134 rotates to locate the second connection point 132a at a farthest position of the second connection point 132a relative to the channel 111. When the first gear 133 rotates to locate the first connection point 131a at a farthest position of the first connection point 131a relative to the channel 111, the second gear 134 rotates to locate the second connection point 132a at a nearest position of the second connection point 132a relative to the channel 111. In this way, the two linkage units 140 move along the channel 111 in a reciprocating manner.

Furthermore, since the linkage units 140 are driven by the first gear assembly 130 to move along the channel 111 in a reciprocating manner, the two blades 150 respectively connected to the linkage units 140 are driven to move in a reciprocating manner as well. Consequently, since the two linkage units 140 are driven by the same output gear 121 and through the same gear ratio between the output gear 121 and the first gear 133 and between the output gear 121 and the second gear 134, the forces of the blades 150 acting on the bone 200 are the same in magnitude but opposite in direction. In this way, during an operation, the forces acting on the bone 200 by each of the two blades 150 cancel out with each other, such that the net resultant force acting on the bone 200 by the rasp 100 is zero. As a result, the surgeon can have a better control over the use of the rasp 100. Consequently, the safety of operation is obviously increased. For example, the risk of fracturing the proximal femur by the rasp 100 during operation can be significantly reduced.

In this embodiment, the output gear 121 has a second pitch center diameter PCD2 smaller than the first pitch center diameters PCD1 of the first gear 133 and the second gear 134. Therefore, the forces acting on the linkage units 140 respectively by the first gear 133 and the second gear 134 are increased in magnitude while decreased in speed relative to the output gear 121. As a result, the surgeon can have a better control over the use of the rasp 100. Consequently, the safety of operation is obviously increased.

In addition, in structural point of view for the rasp 100, there are only a small number of moving parts involved. Thus, the chance that any of the moving parts gets failed is relatively low, and the maintenance time and cost of the rasp 100 is significantly decreased.

Furthermore, as the blades 150 are detachably connected to the second ends 140b of the linkage units 140, the blades 150 can be simply detached from the linkage units 140 and arranged for sterilization. Therefore, sterilization of the blades 150 between every operation can be conveniently carried out. Thus, the risk of bacterial infection and contamination of the blades 150 is greatly reduced.

To be more specific about the structure of the linkage units 140, each of the linkage units 140 includes a connecting rod 141 and an arm 142. Each of the first ends 140a is located on the corresponding connecting rod 141. The connecting rods 141 are located between the first gear 133 and the second gear 134. Each of the arms 142 is connected with the corresponding connecting rod 141 and passes through the channel 111. Thus, the channel 111 provides guidance to the sliding movement of the arms 142. Each of the second ends 140b is located on the corresponding arm 142 away from the connecting rods 141.

Figure 5:
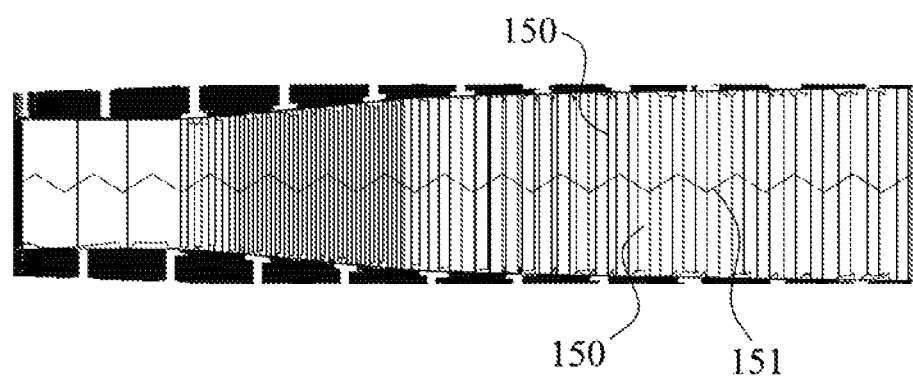
FIG. 5 is a bottom view of the blades of the rasp of FIG. 1.

FIG. 5 is a bottom view of the blades 150 of the rasp 100 of FIG. 1. As shown in FIG. 5, each of the blades 150 has a plurality of grooves 151 parallel to each other. The grooves 151 of one of the blades 150 are slidably engaged with the grooves 151 of another one of the blades 150. Therefore, apart from the guidance of the channel 100 to the sliding movement of the arms 142 of the linkage units 140, the grooves 151 can further help to avoid the risk that the two blades 150 have lateral movements with each other.

As shown in FIGS. 3-4, the driving mechanism includes a power source 122 and a motor 123. The motor 123 is electrically connected to the power source 122 and includes an output shaft 123a connected to the output gear 121, so as to drive the output shaft 123a to rotate the output gear 121. In this embodiment, the power source 122 is a rechargeable battery. However, this choice of the power source 122 does not limit the present disclosure.

Figure 6:
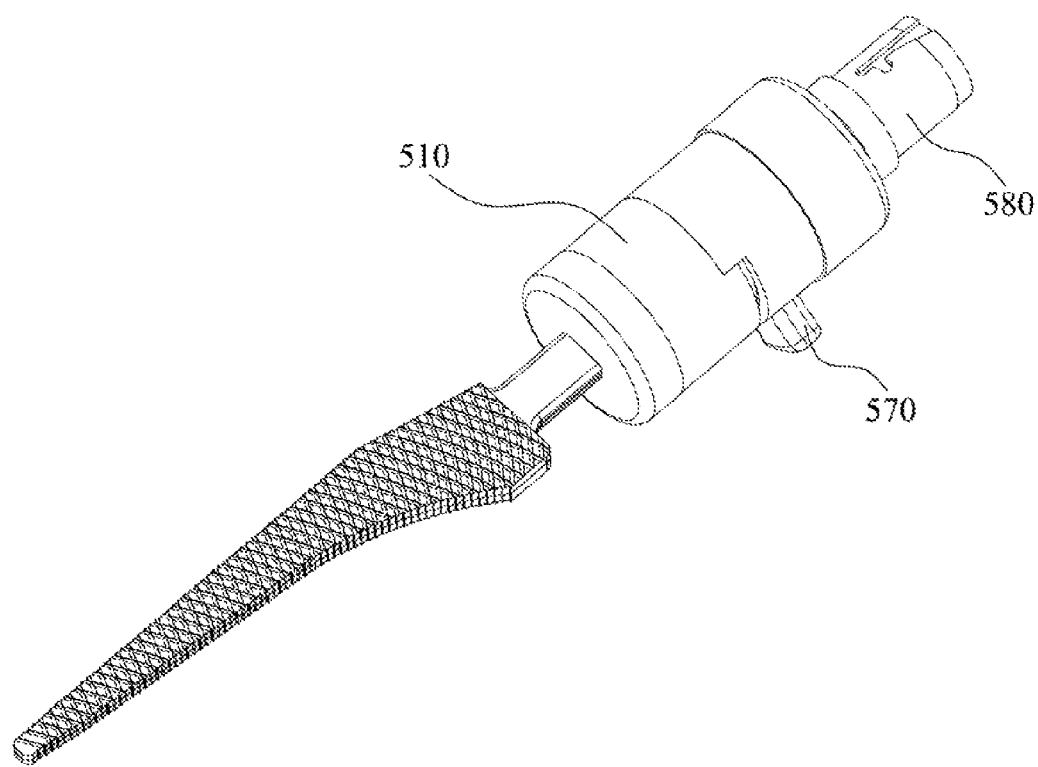
FIG. 6 is a perspective diagram of a rasp according to another embodiment of the present disclosure.
Figure 7:
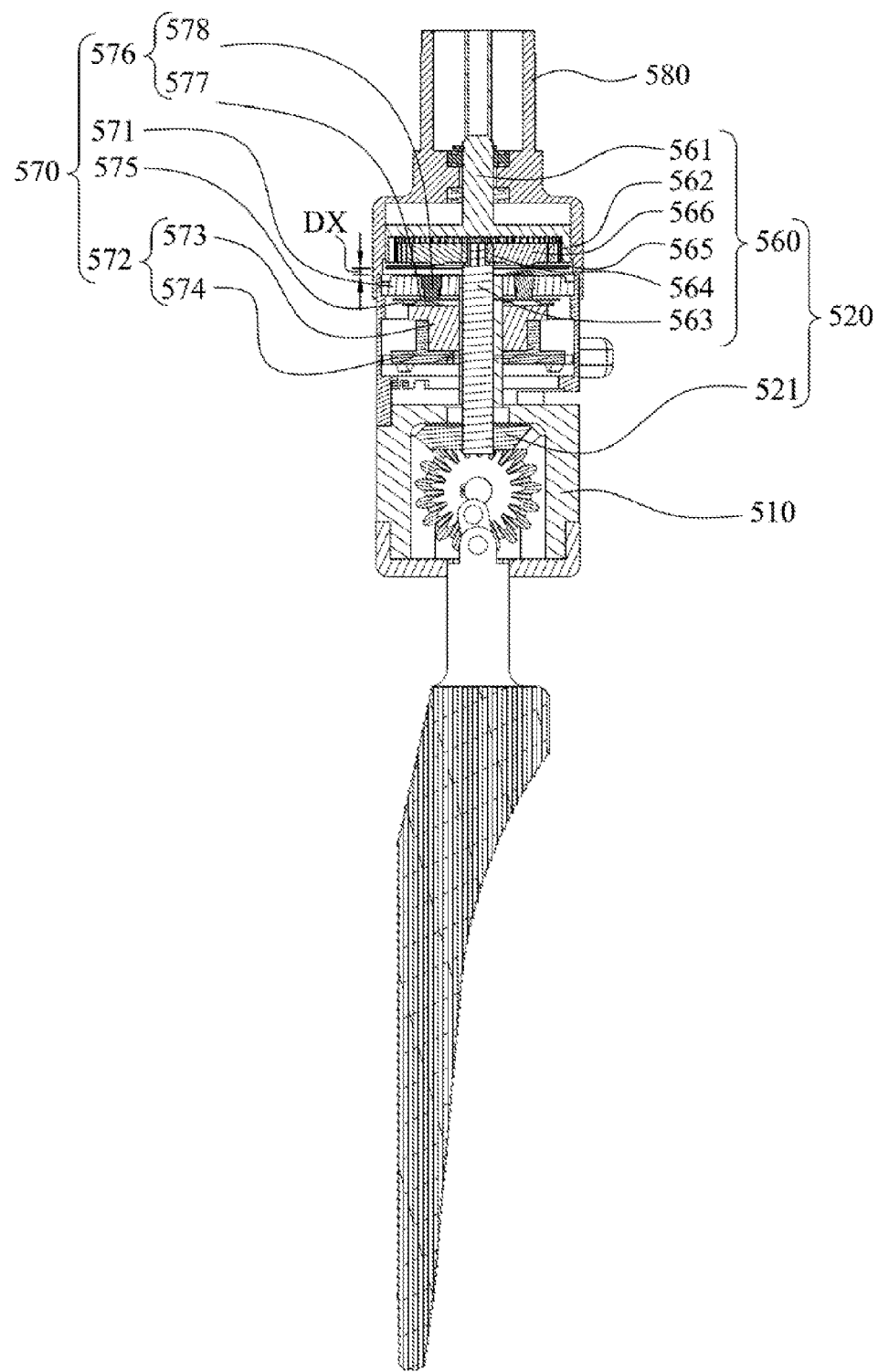
FIG. 7 is a sectional view of the rasp of FIG. 6.
Figure 8:
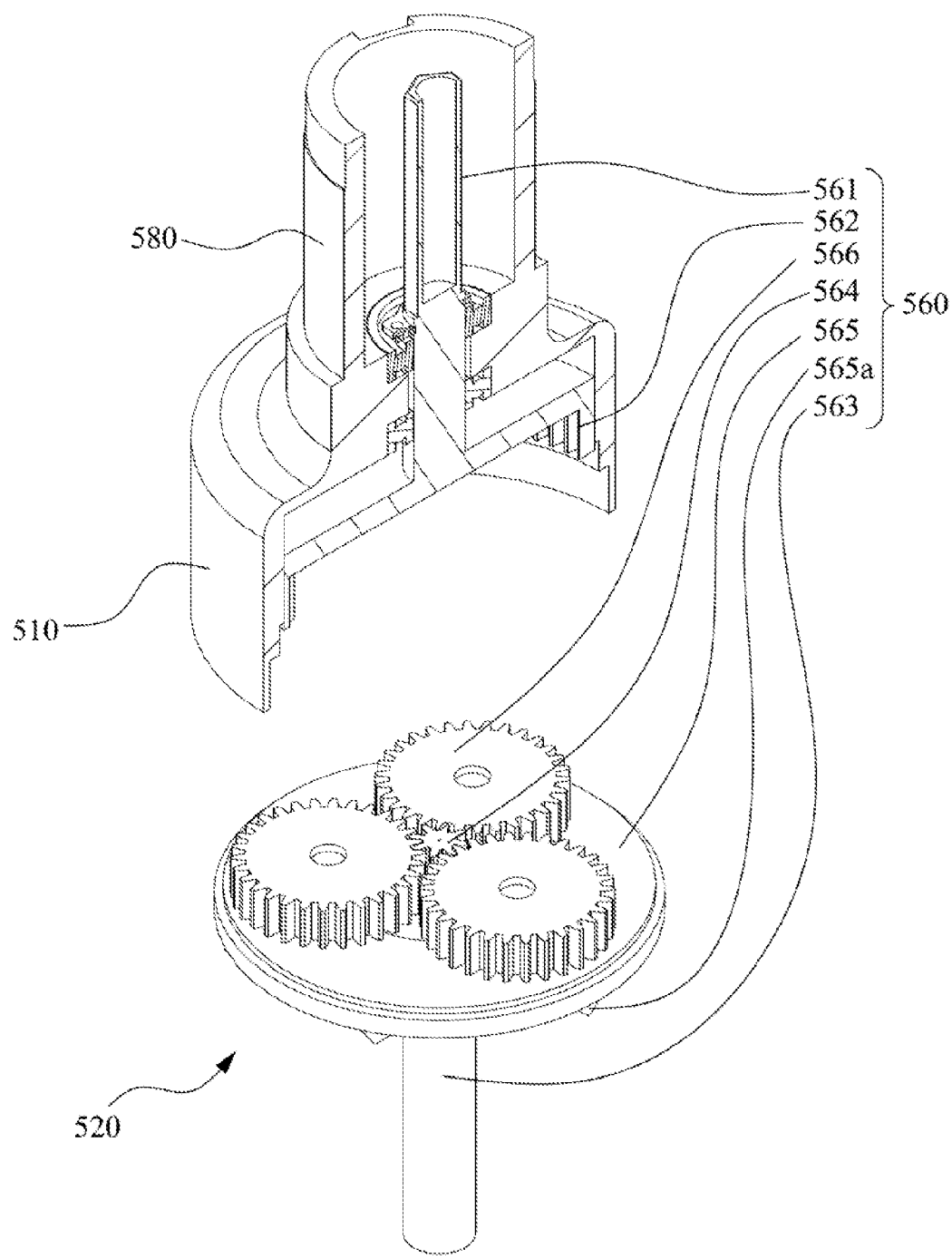
FIG. 8 is a partially exploded perspective view of the rasp of FIG. 6, illustrating a second gear assembly.
Figure 9:
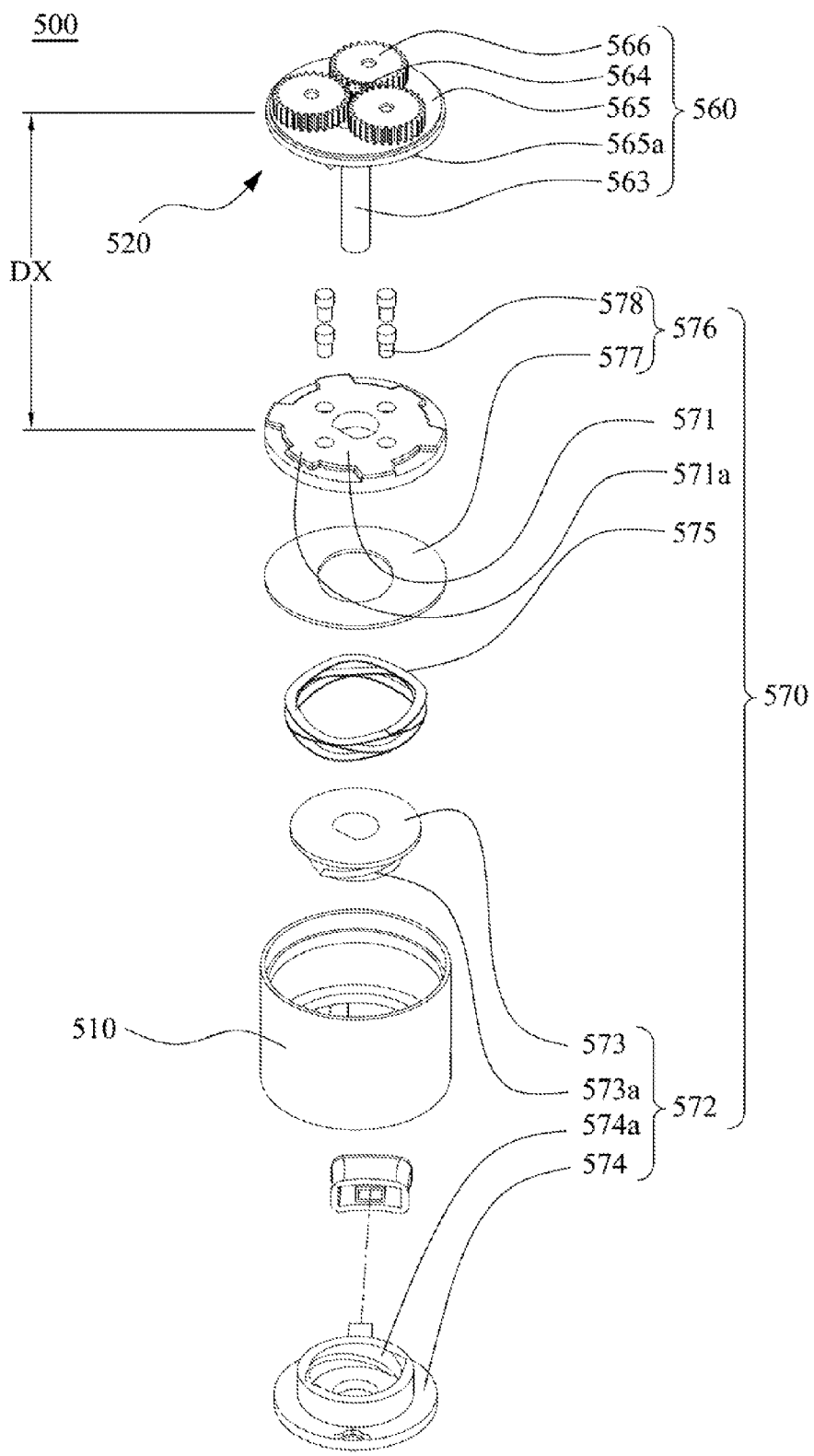
FIG. 9 is a partially exploded perspective view of the rasp of FIG. 6, illustrating a torque limiter.

FIG. 6 is a perspective diagram of a rasp 500 according to another embodiment of the present disclosure. FIG. 7 is a sectional view of the rasp 500 of FIG. 6. FIG. 8 is a partially exploded perspective view of the rasp 500 of FIG. 6, illustrating a second gear assembly 560. FIG. 9 is a partially exploded perspective view of the rasp 500 of FIG. 6, illustrating a torque limiter 570. As shown in FIGS. 6-9, the driving mechanism 520 includes the second gear assembly 560. The second gear assembly 560 includes an input shaft 561, an annulus gear 562, an output shaft 563, a sun gear 564, a planetary gear platform 565 and a plurality of planet gears 566. The input shaft 561 is substantially coaxial with the first axis X1, and is configured to be driven by an external driving device (not shown). The annulus gear 562 is connected to the input shaft 561 in which a center of rotation of the annulus gear 562 is on the first axis X1. The output shaft 563 is connected to the output gear 521 and coaxial with the first axis X1. The sun gear 564 is connected to and coaxial with the output shaft 563. The output shaft 563 passes through the planetary gear platform 565. The output gear 521 and the sun gear 564 are respectively located at two opposite sides of the planetary gear platform 565. The planetary gear platform 565 has a plurality of first protruding portions 365a located on the side facing the output gear 521. The planet gears 566 are rotatably mounted on the planetary gear platform 565, in which the planet gears 566 are located between the input shaft 561 and the planetary gear platform 565 and between the annulus gear 562 and the sun gear 564. Each of the planet gears 566 is meshed with the annulus gear 562 and the sun gear 564.

As shown in FIGS. 6-7 and 9, the rasp 500 further includes a torque limiter 570. The torque limiter 570 is connected with the housing 510 and includes a locking plate 571 and an adjustment assembly 572. The locking plate 571 is located between the output gear 521 and the planetary gear platform 565, in which the output shaft 563 passes through the locking plate 571. The locking plate 571 has a plurality of second protruding portions 571a facing the side on which the first protruding portions 365a are located. The adjustment assembly 572 is operatively connected to the planetary gear platform 565 for moving the planetary gear platform 565 towards or away from the locking plate 571, such that a distance DX between the locking plate 571 and the planetary gear platform 565 can be adjusted.

Under the adjustment of the distance DX between the locking plate 571 and the planetary gear platform 565 by the operation of the adjustment assembly 572, a torque limiting threshold is set for the torque limiter 570 according to the degree of interference between the first protruding portions 565a and the second protruding portions 571a. When the external driving device drives the input shaft 561 with a driving torque below the torque limiting threshold, the annular gear 562 rotates while the planetary gear platform 565 does not rotate. Thus, the planet gears 566 rotate about their respective axis, and consequently the sun gear 564 rotates at a multiplied rotational speed relative to the annulus gear 562. On the other hand, when the external driving device drives the input shaft 561 with a driving torque above the torque limiting threshold, the planetary gear platform 565 rotates with the annular gear 562, the planet gears 566 rotate about the sun gear 564, such that the sun gear 564 remains stationary and does not rotate. In this way, the rasp 500 is protected from damage by an excessive driving torque from the external driving device.

To be more specific, the adjustment assembly 572 includes a first adjustment structure 573 and a second adjustment structure 574. The first adjustment structure 573 is operatively connected to the planetary gear platform 565 and has a first threaded portion 573a, in which the locking plate 571 is located between the first adjustment structure 573 and the planetary gear platform 565. The second adjustment structure 574 is rotatably connected with the housing 510 and has a second threaded portion 574a meshed with the first threaded portion 573a, in which the first adjustment structure 573 is located between the locking plate 571 and the second adjustment structure 574. When the second adjustment structure 574 rotates relative to the housing 510 to move the first adjustment structure 573 towards the locking plate 571, the planetary gear platform 565 is driven by the first adjustment structure 573 to correspondingly move away from the locking plate 571. When the second adjustment structure 574 rotates relative to the housing 510 to move the first adjustment structure 573 away from the locking plate 571, the planetary gear platform 565 is driven by the first adjustment structure 573 to correspondingly move towards the locking plate 571, so as to adjust the distance DX between the planetary gear platform 565 and the locking plate 571.

In addition, as shown in FIGS. 7 and 9, the torque limiter 570 further includes a spring 575 and a pushing structure 576. The spring 575 is located between the first adjustment structure 573 and the locking plate 571. The pushing structure 576 is located between the spring 575 and the locking plate 571. The pushing structure 576 includes a base plate 577 and a supporting pillar 578 connected to the base plate 577, in which the supporting pillar 578 passes through the locking plate 571 and abuts against the planetary gear platform 565. The spring 575 acts to control the sensitivity of the responsive movement of the pushing structure 576 relative to the planetary gear platform 565, upon different requirements of the surgeons.

In this embodiment, as shown in FIGS. 6-8, the rasp 500 further includes an adaptor 580 connected to the housing 510. The adaptor 580 is configured to engage with the external driving unit and the external driving unit drives the input shaft 561 to rotate relative to the housing 510. For example, the adaptor 580 can be a Hudson chuck adaptor and the external driving unit is a standard Hudson drill. The Hudson chuck adaptor allows the rasp 500 to engage with the standard Hudson drill and work in conjunction with any standard drill that operates with a Hudson drill trinkle. It is noted that the type of the adaptor 580 as a Hudson chuck adaptor as cited herein is only illustrative and is not to limit the claimed scope. A person having ordinary skill in the art of the present invention should flexibly choose the type of the adaptor 580.

Figure 10:
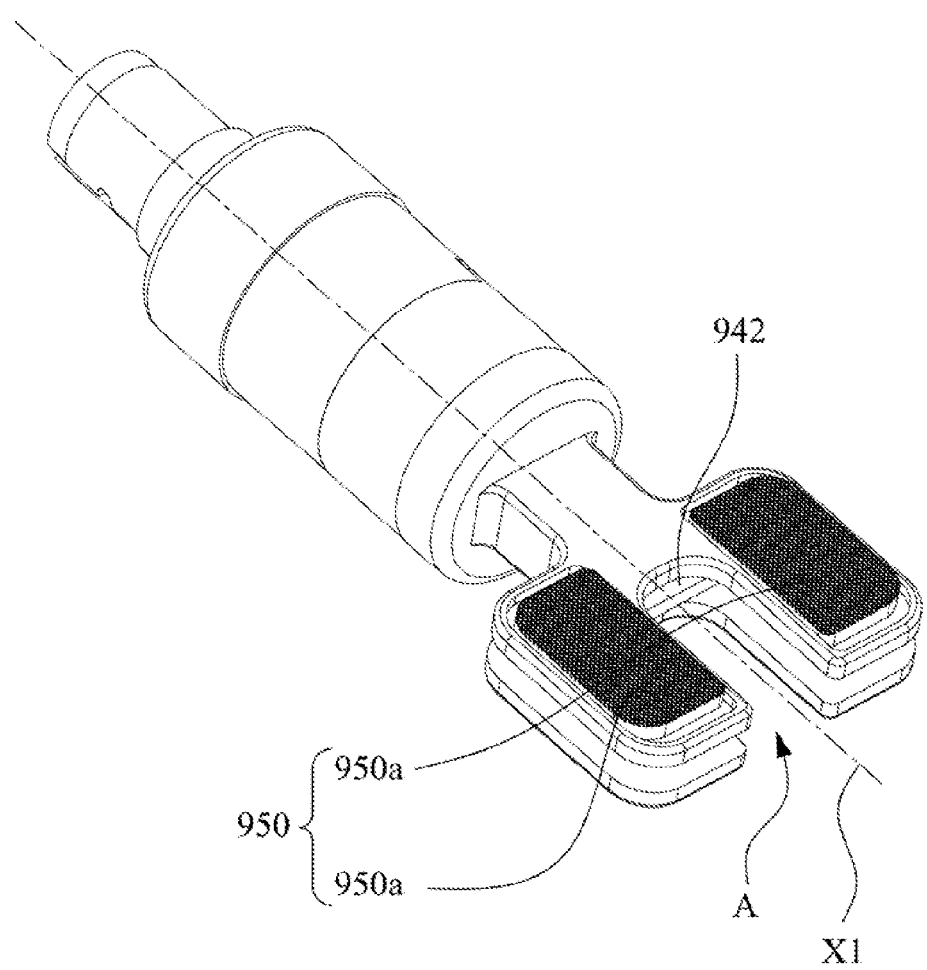
FIG. 10 is a perspective diagram of a rasp according to a further embodiment of the present disclosure.
Figure 11:
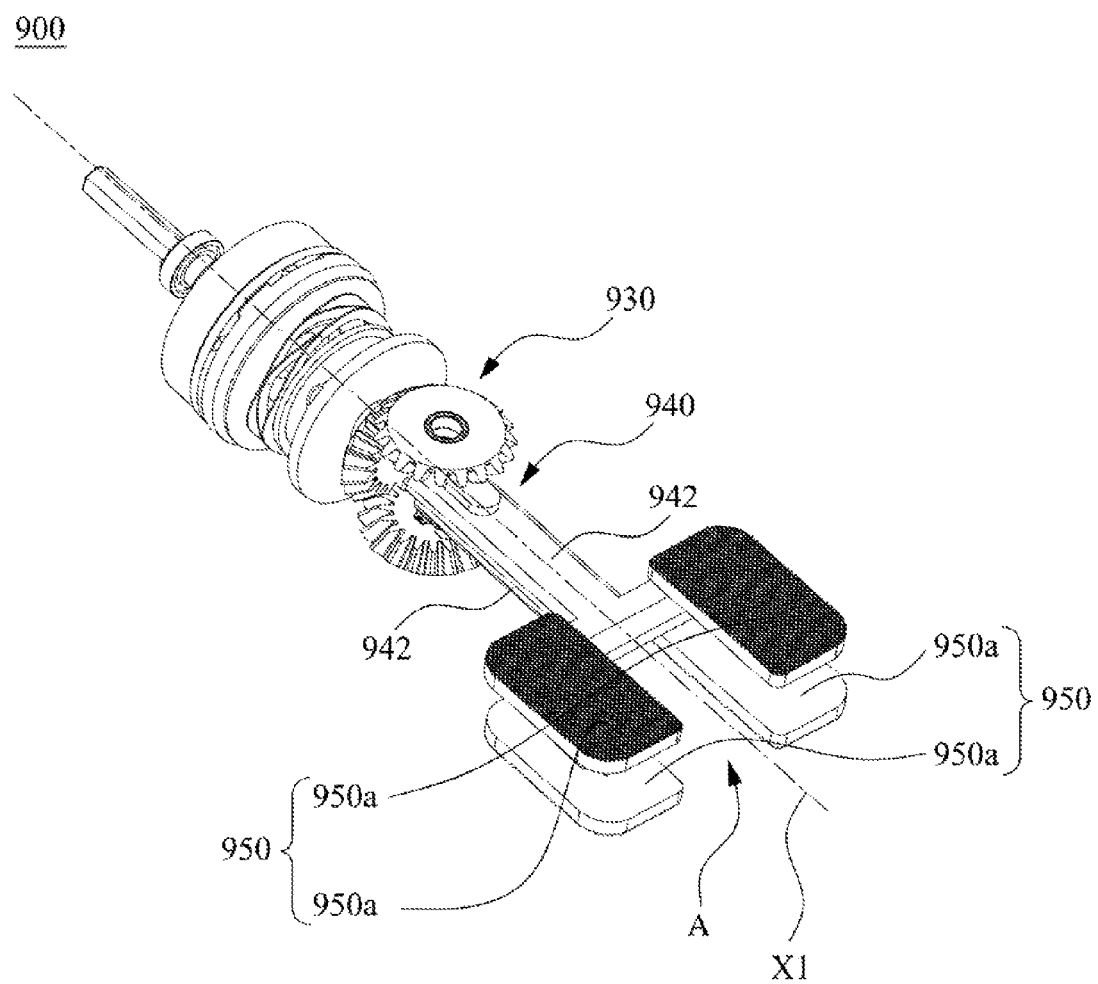
FIG. 11 is a partially exploded perspective view of the rasp of FIG. 10.

FIG. 10 is a perspective diagram of a rasp 900 according to a further embodiment of the present disclosure. FIG. 11 is a partially exploded perspective view of the rasp 900 of FIG. 10. As shown in FIGS. 10-11, each of the blades 950 includes two sub-blades 950a, such that an accommodation space A is formed between the sub-blades 950a and along the first axis X1. Similar to the previous embodiments, the arms 942 of the linkage units 940 are driven by the first gear assembly 930 to move in a reciprocating manner with each other along the first axis X1. Thus, the blades 950 connected to the arms 942 move in a reciprocating manner with each other along the first axis X1 as well. As the accommodation space A formed between the sub-blades 950a is located along the first axis X1, the accommodation space A is not interfered by the reciprocating movements of the sub-blades 950a. As a result, in the practical application for a surgery at a knee, the rasp 900 can be used to insert between the distal end of the femur and the proximal end of the tibia (not shown) even though there exist an anterior cruciate ligament and a posterior ligament. The anterior cruciate ligament and the posterior ligament are accommodated in the accommodation space A. Moreover, in such an orientation of the rasp 900 relative to the femur and the tibia, an even gap between the femur and the tibia can be created and balanced by the rasp 900.

In summary, when compared with the prior art, the embodiments of the present disclosure mentioned above have at least the following advantages:

(1) In the embodiments of the present disclosure, the linkage units are driven by the first gear assembly to move along the channel in a reciprocating manner. Therefore, the two blades respectively connected to the linkage units are driven to move in a reciprocating manner as well. In this way, during an operation, the forces acting on the bone by each of the two blades cancel out with each other, such that the net resultant force acting on the bone by the rasp is zero. As a result, the surgeon can have a better control over the use of the rasp. Consequently, the safety of operation is obviously increased.

(2) In the embodiments of the present disclosure, there are only a small number of moving parts involved. Thus, the chance that any of the moving parts gets failed is low, and the maintenance time and cost of the rasp is significantly decreased.

(3) In the embodiments of the present disclosure, the output gear has a second pitch center diameter smaller than the first pitch center diameters of the first gear and the second gear. Therefore, the forces acting on the linkage units respectively by the first gear and the second gear are increased in magnitude while decreased in speed relative to the output gear. As a result, the surgeon can have a better control over the use of the rasp. Consequently, the safety of operation is obviously increased.

(4) In the embodiments of the present disclosure, the linkage units slidably pass through the channel. Thus, the reciprocating movements of the linkage units along the sliding direction can be simply guided by the channel. In addition, each of the blades has a plurality of grooves parallel to each other, and the grooves of one of the blades are slidably engaged with the grooves of another one of the blades. As a result, the risk that the two blades have lateral movements with each other is safely avoided.

Although the present disclosure has been described in considerable detail with reference to certain embodiments thereof, other embodiments are possible. Therefore, the spirit and scope of the appended claims should not be limited to the description of the embodiments contained herein.

It will be apparent to the person having ordinary skill in the art that various modifications and variations can be made to the structure of the present disclosure without departing from the scope or spirit of the present disclosure. In view of the foregoing, it is intended that the present disclosure cover modifications and variations of the present disclosure provided they fall within the scope of the following claims.

What is claimed is:

1. A rasp for shaping a bone for receiving a prosthesis, the rasp comprising:
    a housing having a channel orientated along a first axis;
    a driving mechanism having an output gear rotating about the first axis;
    a first gear assembly rotatably disposed in the housing to rotate about a second axis and driven by the output gear, the first gear assembly having a first rotation surface and a second rotation surface opposite to each other and a first connection point and a second connection point respectively located on the first and second rotation surfaces;
    two linkage units slidably passing through the channel, each of the linkage units having a first end and a second end, wherein the first end of each of the linkage units is pivotally connected to a corresponding one of the first and second connection points, such that the second ends are driven by the first gear assembly to move along the first axis in a reciprocating manner; and
    two blades respectively and detachably connected to the second ends.

2. The rasp of claim 1, wherein the first gear assembly comprises:
    a first gear rotatably disposed in the housing and driven by the output gear, such that the first gear rotates in a first direction about the second axis, wherein the first rotation surface is located on the first gear; and
    a second gear rotatably disposed in the housing and driven by the output gear, such that the second gear rotates in a second direction opposite to the first direction about the second axis, wherein the second rotation surface is located on the second gear.

3. The rasp of claim 2, wherein a rotation locus of the first connection point and a rotation locus of the second connection point are 180 degrees out of phase, such that when the first gear rotates to locate the first connection point at a nearest position of the first connection point relative to the channel, the second gear rotates to locate the second connection point at a farthest position of the second connection point relative to the channel, and when the first gear rotates to locate the first connection point at a farthest position of the first connection point relative to the channel, the second gear rotates to locate the second connection point at a nearest position of the second connection point relative to the channel.

4. The rasp of claim 2, wherein the first gear and the second gear have a same first pitch center diameter.

5. The rasp of claim 4, wherein the output gear has a second pitch center diameter smaller than the first pitch center diameter.

6. The rasp of claim 2, wherein each of the linkage units comprises:
a connecting rod, each of the first ends being located on the corresponding connecting rod, the connecting rods being located between the first gear and the second gear; and
an arm connected with the corresponding connecting rod and passing through the channel, each of the second ends being located on the corresponding arm away from the connecting rods.

7. The rasp of claim 1, wherein each of the blades has a plurality of grooves parallel to each other, the grooves of one of the blades are slidably engaged with the grooves of another one of the blades.

8. The rasp of claim 1, wherein each of the blades comprises two sub-blades, such that an accommodation space is formed between the sub-blades and along the first axis.

9. The rasp of claim 1, wherein the driving mechanism comprises:
a power source; and
a motor electrically connected to the power source and comprising an output shaft connected to the output gear, so as to drive the output shaft to rotate the output gear.

10. The rasp of claim 9, wherein the power source is a rechargeable battery.

11. The rasp of claim 1, wherein the driving mechanism comprises a second gear assembly, the second gear assembly comprises:
an input shaft substantially coaxial with the first axis, and configured to be driven by an external driving device;
an annulus gear connected to the input shaft, wherein a center of rotation of the annulus gear is on the first axis;
an output shaft connected to the output gear and coaxial with the first axis;
a sun gear connected to and coaxial with the output shaft;
a planetary gear platform, wherein the output shaft passes through the planetary gear platform, the output gear and the sun gear are respectively located at two opposite sides of the planetary gear platform, and the planetary gear platform has a plurality of first protruding portions located on the side facing the output gear; and
a plurality of planet gears rotatably mounted on the planetary gear platform, wherein the planet gears are located between the input shaft and the planetary gear platform and between the annulus gear and the sun gear, each of the planet gears is meshed with the annulus gear and the sun gear.

12. The rasp of claim 11, further comprising a torque limiter connected with the housing and comprising:
a locking plate located between the output gear and the planetary gear platform, wherein the output shaft passes through the locking plate, the locking plate has a plurality of second protruding portions facing the side on which the first protruding portions are located; and
an adjustment assembly operatively connected to the planetary gear platform for moving the planetary gear platform towards or away from the locking plate, such that a distance between the locking plate and the planetary gear platform can be adjusted.

13. The rasp of claim 12, wherein the adjustment assembly comprises:
a first adjustment structure operatively connected to the planetary gear platform and having a first threaded portion, wherein the locking plate is located between the first adjustment structure and the planetary gear platform; and
a second adjustment structure rotatably connected with the housing and having a second threaded portion meshed with the first threaded portion, wherein the first adjustment structure is located between the locking plate and the second adjustment structure, and when the second adjustment structure rotates relative to the housing to move the first adjustment structure towards the locking plate, the planetary gear platform is driven by the first adjustment structure to correspondingly move away from the locking plate, when the second adjustment structure rotates relative to the housing to move the first adjustment structure away from the locking plate, the planetary gear platform is driven by the first adjustment structure to correspondingly move towards the locking plate, so as to adjust the distance.

14. The rasp of claim 13, wherein the torque limiter further comprises:
a spring located between the first adjustment structure and the locking plate; and
a pushing structure located between the spring and the locking plate, the pushing structure comprising a base plate and a supporting pillar connected to the base plate, wherein the supporting pillar passes through the locking plate and abuts against the planetary gear platform.

15. The rasp of claim 11, further comprising an adaptor connected to the housing, the adaptor being configured to engage with the external driving unit and the external driving unit drives the input shaft to rotate relative to the housing.

* * * * *